United States Patent [19]

Svoboda

[11] 4,309,431

[45] Jan. 5, 1982

[54] METHOD OF INHIBITING GROWTH OF TUMOR CELLS

[75] Inventor: Gordon H. Svoboda, Indianapolis, Ind.

[73] Assignee: Eli Lilly and Company, Indianapolis, Ind.

[21] Appl. No.: 843,776

[22] Filed: Oct. 20, 1977

Related U.S. Application Data

[60] Continuation of Ser. No. 720,711, Aug. 7, 1976, abandoned, which is a division of Ser. No. 374,588, Jun. 28, 1973, Pat. No. 3,985,899, which is a continuation of Ser. No. 268,406, Jul. 3, 1972, abandoned, which is a continuation-in-part of Ser. No. 46,811, Jun. 16, 1970, abandoned, which is a continuation-in-part of Ser. No. 840,114, Jun. 18, 1969, abandoned, which is a continuation-in-part of Ser. No. 536,905, Mar. 23, 1966, abandoned.

[51] Int. Cl.³ .......................................... A61K 31/435

[52] U.S. Cl. ................................................. 424/257
[58] Field of Search ...................................... 424/257

[56] References Cited

PUBLICATIONS

Chemical Abstracts 45:5696(e) (1951).
Chemical Abstracts 45:9369(f) (1951).
Chemical Abstracts 47:3862(b) (1953).

*Primary Examiner*—Jerome D. Goldberg
*Attorney, Agent, or Firm*—James L. Rowe; Arthur R. Whale

[57] ABSTRACT

This invention relates to a novel process for inhibiting the growth of malignant tumor cells in mammals, particularly the growth of multiple myeloma in humans, employing the alkaloid acronycine as the inhibiting agent.

4 Claims, 1 Drawing Figure

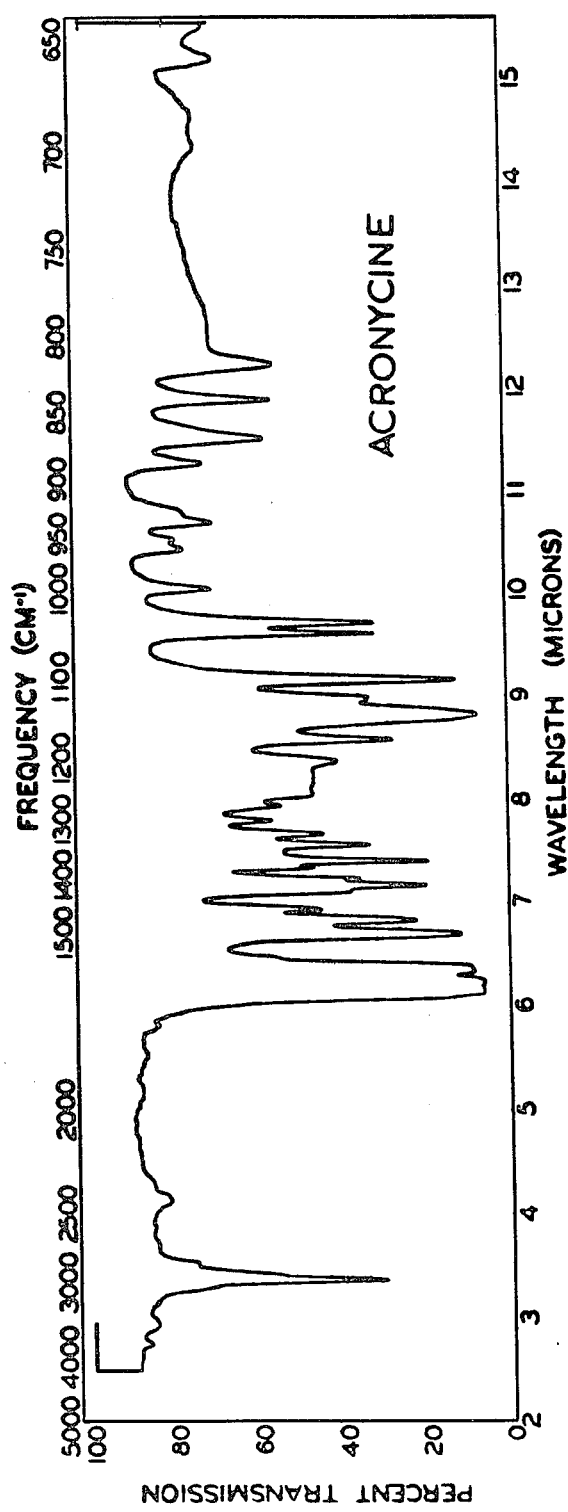

METHOD OF INHIBITING GROWTH OF TUMOR CELLS

CROSS-REFERENCE

This application is a continuation of my copending application Ser. No. 720,711 filed Aug. 7, 1976, now abandoned, which was a division of application Ser. No. 374,588, filed June 28, 1973, now U.S. Pat. No. 3,985,899, which was a continuation of application Ser. No. 268,406, filed July 3, 1972, now abandoned, which was a continuation-in-part of my copending application Ser. No. 46,811, filed June 16, 1970, now abandoned, which was a continuation-in-part of my then copending application Ser. No. 840,114, filed June 18, 1969, now abandoned, which was a continuation-in-part of my then copending application, Ser. No. 536,905, filed Mar. 23, 1966, now abandoned.

BACKGROUND OF THE INVENTION

Most of the agents useful in inhibiting the growth of malignant tumor cells discovered to date have either been alkylating agents, of the nature of the nitrogen mustards, or anti-metabolites for vitamins and nucleic acids, such as 8-azaguanine, 5-fluoronicotinic acid, and the like. Recently a group of novel alkaloids, obtainable in pure form from the plant Vinca Rosea, have been found to be particularly valuable in the treatment of leukemias and have even shown some activity against various solid tumors. These alkaloids have a chemical structure which is totally unrelated to any known anti-tumor agent, and they apparently act in a manner distinctly different from such other agents.

It is an object of this invention to provide a method of inhibiting the growth of malignant tumor cells in mammals, specifically mice, which method employs a previously known alkaloid not related structurally to the Vinca alkaloids and having a quite different anti-tumor spectrum when compared with that of any of the anti-tumor agents heretofore known.

SUMMARY OF THE INVENTION

In fulfillment of the above and other objects, this invention provides a method of inhibiting the growth of malignant tumor cells which comprises administering to a mouse, in whose body the malignant tumor is present and proliferating, an effective quantity of the alkaloid acronycine represented by the following formula:

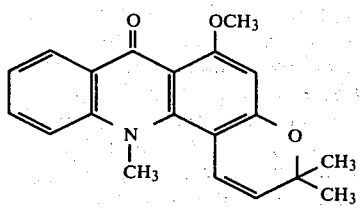

Acronycine, among other alkaloids, was obtained originally in small quantity, from the bark of the Australian scrub ash or scrub yellow wood, Acronychia Baueri Schott, (also known as Bauerella Australiana Borzi) by Lahey and co-workers [Australian J. Sci. Res., 2A 423-b (1949)]. A description of the physical properties of the purified material is given in ibid, 3A, 593-614 (1950). The following preparation illustrates my method of obtaining acronycine from Achronychia Baueri Schott bark:

Preparation of Acronycine

About 1.5 kg. of coarsely ground bark of the Australian scrub ash, Acronychia Baueri Schott, were stirred with two 3.5-liter portions of n-hexane in order to extract fatty material present therein. The defatted bark was then extracted with three 4-liter portions of diethyl ether. The ether extracts were combined, and the combined extracts were concentrated in vacuo to a volume of about 1 liter. Upon cooling, about 11.5 g of yellow-gold crystals precipitated from the concentrate. These crystals were separated by filtration, and were proven to be a mixture of the known alkaloids acronycine and melicopine by means of x-ray, ultraviolet, and infrared spectra and by thin layer chromatography. Recrystallization of the crystal mixture from methanol, employed at the rate of 10 ml. of methanol per gram of crystals, yielded four successive crops of crystals as follows: 1.29 g. of melicopine; 2.60 g. of slightly impure acronycine; 1.39 g. of a mixture of acronycine and melicopine; and 1.69 g. of slightly impure acronycine. The second and fourth crystal fractions, which were substantially pure acronycine, were combined and recrystallized from methanol at the rate of about 8 ml. per gram of crystalline material. About 4.14 g. of acronycine were obtained thereby. Acronycine thus purified was one-spot material upon thin-layer chromatography; i.e., contained no other alkaloids.

Properties of Acronycine

Pure acronycine produced as above had the following physical characteristics:

Crystals

The crystals obtained from methanol were opaque yellow coarse particles whose precise crystalline form could not be determined. The crystals obtained from ethanol were clear yellow needles occurring in fan-shaped clumps. The crystals from acetone were monoclinic rods.

Melting Point

Acronycine had the following melting point: 174°–176° C.

Elemental Analysis

Calcd. for $C_{20}H_{19}NO_3$: C, 74.74; H, 5.96; N, 4.36; O, 14.94. Found: C, 74.76; H, 6.19; N, 4.29; O, 15.01.

Ultraviolet Spectrum

The ultraviolet spectrum had peaks at the following wave lengths with the extinction coefficient for each peak given immediately thereafter in parentheses:
$\lambda$max (EtOH)=280 m$\mu$ (log $\epsilon$=4.60), 291 m$\mu$ (log $\epsilon$=4.54), 304 m$\mu$ (log $\epsilon$=4.28), 392 m$\mu$ (log $\epsilon$=3.84).

Infrared Spectrum

The infrared spectrum of acronycine is given in FIG. I.

X-Ray Crystallography

The following table gives x-ray crystallography data for acronycine. The table lists the wave length, d, at which absorption occurs, and the intensity, $I/I_1$, of the particular band:

TABLE I

| d | $I/I_1$ | d | $I/I_1$ | d | $I/I_1$ | d | $I/I_1$ |
|---|---|---|---|---|---|---|---|
| 9.85 | 1.00b | 5.67 | .15 | 4.10 | .06 | 3.57 | .02 |
| 7.36 | .06 | 5.48 | .20 | 4.02 | .06 | 3.41 | .30 |
| 6.88 | .30 | 5.29 | .15 | 3.88 | .08 | 3.18 | .30 |
| 6.50 | .06 | 4.80 | .15 | 3.72 | .04 | 3.01 | .04 |
| 5.87 | .20 | 4.50 | .06b | 3.64 | .75 | 2.91 | .06b |
| 2.70 | .02 | 2.25 | .04 | 2.01 | .02 | | |
| 2.64 | .02 | 2.15 | .02 | 1.99 | .02 | | |
| 2.53 | .02 | 2.14 | .02 | 1.86 | .02 | | |
| 2.33 | .04 | 2.07 | .04 | | | | |
| 2.28 | .02 | 2.05 | .04 | | | | |

Acronycine has shown excellent anti-tumor activity against the following varieties of transplanted tumors in mice: adenocarcinoma, Ad-775: plasma cell myeloma, X-5563; Mecca lymphosarcoma, MLS; B-82 leukemia; C-1498 myelogenous leukemia; Sarcoma 180; Ridgeway osteogenic sarcoma; Shionogi carcinoma 115; and high-malignancy alone. Indefinite survivors, mice which survive 45 days or longer after inoculation with the tumor cells in the case of leukemias, or who survive indefinitely after transplantation of the tumor cells in the case of sarcomas or carcinomas, have been found with each of the above tumors, after treatment for 10 days with acronycine. The C-1498 myelogenous leukemia and Mecca lymphosarcoma are both metastasizing tumors in mice. Acronycine is the first alkaloid found to adversely affect the progress of the transplanted tumor C-1498 myelogenous leukemia. With the plasma cell myeloma, X-5563, there is an abnormal protein found in the $\tau$-globulin fraction of the blood of mice bearing this tumor. Treatment with acronycine has produced not only an inhibition of the X-5563 myeloma with a decrease in tumor size in all animals, plus 8 out of 10 indefinite survivors in one test, but also has decreased the amount of the abnormal protein in the blood.

Another interesting activity of acronycine is its effectiveness against the Shionogi carcinoma 115. This carcinoma is an androgen-dependent tumor, and in mice there is found a 100 percent inhibition of the tumor with indefinite survivors. Treatment in the case of the mice implanted with Shionogi carcinoma 115 was begun 5 days after transplantation.

Acronycine has demonstrated its anti-tumor activity when administered to mice by the oral, intraperitioneal, intravenous and subcutaneous routes; the compound is administered orally either in a telescoping gelatin capsule or as a pill after admixing with customary pill-making ingredients. For intraperitioneal or subcutaneous administration, the compound is ground with Emulphor (a polyoxyethylated fatty acid which is water miscible and nontoxic when diluted 1:10 with either sterile water or sterile physiological saline solution). The Emulphor suspension is administered as such or can be diluted with water. For intravenous administration, the Emulphor suspension is diluted 1:10 with physiological saline.

If an oral dosage form is to be used, the nature of the excipient is most important in that, with certain excipients such as talc, there is a lowered absorption of the drug from the intestinal tract. I prefer to use an excipient such as starch which does not interfere with drug absorption in the intestine. In addition, there is better absorption of acronycine if the drug is micronized before mixing with starch. In fact, a preferred preparation of our dosage form is one in which a solution of the drug is sprayed onto the starch or slurried with the starch. In each case, the solvent is removed by evaporation. The acronycine is present in an amorphous form on the starch.

The following preparations will serve to illustrate the novel pharmaceutical corporation in unit dosage form for oral administration useful in the tumor-suppressing process of this invention.

PREPARATION I 0.5 g. of micronized acronycine (90 percent of the acronycine had a size of 10 microns or less) was mixed thoroughly with 2.29 g. of starch. The empty telescoping gelatin capsules were filled with 0.27 g. each of the above mixture.

PREPARATION II 0.5 g. of acronycine were dissolved in 250 ml. of ethylenedichloride. The resulting solution was slurried with 2.5 g. of starch and the solvent removed by evaporation. Empty telescoping gelatin capsules were filled with 0.30 g. each of the above mixture.

PREPARATION III

Telescoping gelatin capsules were each filled with the following mixture: 100 mg. acronycine, thoroughly milled; 166 mg. lactose; 166 mg. starch; and 8 mg. polyoxyethylene sorbitan monooleate.

Another useful dosage form for administration of acronycine by the oral route comprises a co-precipitate of acronycine and polyvinylpyrrolidone, as described in the patent application of W. D. Walkling, filed June 16, 1970. These acronycine-PVP co-precipitates can be prepared by dissolving each of the components in ethanol, mixing the solutions in such amount as to obtain the desired ratios of acronycine and PVP in the co-precipitate and then removing the solvent by evaporation in vacuo. Particularly useful co-precipitates are those containing 1 part of acronycine to 5 or 10 parts of PVP (M.W.=40,000). These co-precipitates have a markedly greater stability than acronycine itself, being up to 15 to 25 times as soluble.

The customary mode of administration of acronycine to mice is to give the drug at a predetermined dosage level on each of ten successive days. The dosage regimen can vary from 15-100 mg./kg. per day by the intraperitoneal and subcutaneous routes and from 30-80 mg./kg. per day per mouse by the oral route. The toxicity of acronycine marks the upper limit for the daily dose.

Although the standard treatment regimen involves administering the life-prolonging drug to mice 24 hours after the time when the tumor cells are inoculated or transplanted into the mouse, acronycine has the unusual property of being effective in prolongingthe life of tumor-cell inoculated mice when treatment is begun as late as 3, 5 or 6 days after the day of inoculation. This finding is of particular interest with regard to the treatment of C-1498 leukemia, where the percent prolongation of life is still appreciable even though administration of acronycine, by either the intraperitoneal or oral route, is begun as late as 6 days after inoculation with the leukemic cells. Similar results have also been found in treating X-5563 myeloma. It should be noted that ordinarily, untreated mice die from the tumor in a period varying from 14-18 days after inoculation; that is to say, a treatment beginning the sixth day after inoculation could be considered to have begun after one-third to one-half of the life span remaining to the animal has already passed.

Acronycine is administered orally or subcutaneously to humans in dosage amounts varying from 15–2000 mg. per treatment day or at the rate of 50–100 mg./kg. per treatment day, for a period of from 10 to 20 days. A useful dosage regimen for humans consists of 800 mg. per day in 8 divided doses.

The use of acronycine in combating multiple myeloma is shown by the following case histories: A male patient diagnosed as suffering from multiple myeloma was treated with 200 mg. per meter squared of body surface of acronycine per day for 50 days. The patient showed no toxicity from the drug. There was a cessation of pain in the spine and the electrophoretic M protein had decreased 1.5 g. percent.

A second patient was treated for 90 days for multiple myeloma at the same dose rate as above. The patient showed subjective improvement marked by an absence of bone pain. Bony defects noted on X-ray had not changed during the period of treatment.

Little is known about the mechanism of action of acronycine in inhibiting the growth of tumor cells, but it has been ascertained that the compound does not operate via mitotic arrest.

I claim:

1. A method of treating multiple myeloma in humans which comprises administering acronycine to a patient suffering therefrom in an oncolytic amount.

2. A pharmaceutical preparation in dosage unit form adapted for oral administration to achieve an anti-tumor effect in multiple myeloma comprising per dosage unit from 15–100 mgs. of acronycine and from 0.165 to 0.3 g. of starch.

3. A pharmaceutical preparation in accordance with claim 2 in which 90 percent of the acronycine has a particle size of 10 microns or less.

4. A pharmaceutical preparation in accordance with claim 2 in which the acronycine is present in amorphous form.

* * * * *